(12) United States Patent
Bryan et al.

(10) Patent No.: US 7,955,506 B2
(45) Date of Patent: Jun. 7, 2011

(54) PROCESS FOR DEWATERING AN AQUEOUS ORGANIC SOLUTION

(75) Inventors: Paul F. Bryan, Pinole, CA (US);
Shabbir Husain, San Pablo, CA (US);
Prakhar Prakash, San Ramon, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 12/534,669

(22) Filed: Aug. 3, 2009

(65) Prior Publication Data
US 2010/0155331 A1 Jun. 24, 2010

Related U.S. Application Data

(63) Continuation of application No. 12/317,163, filed on Dec. 18, 2008, now abandoned.

(51) Int. Cl.
*B01D 11/00* (2006.01)
*B01D 61/00* (2006.01)

(52) U.S. Cl. ........... 210/644; 210/648; 210/649; 426/11

(58) Field of Classification Search ................. 210/644, 210/49, 650, 652, 195.2, 257.2, 648, 257.266; 426/11
See application file for complete search history.

(56) References Cited

U.S. PATENT DOCUMENTS

| | | | | |
|---|---|---|---|---|
| 3,906,250 A | * | 9/1975 | Loeb | 290/1 R |
| 4,193,267 A | * | 3/1980 | Loeb | 60/649 |
| 4,770,786 A | * | 9/1988 | Manabe et al. | 210/640 |
| 4,781,837 A | * | 11/1988 | Lefebvre | 210/640 |
| 4,816,407 A | * | 3/1989 | Matson | 99/277 |
| 5,098,575 A | * | 3/1992 | Yaeli | 210/652 |
| 5,281,430 A | * | 1/1994 | Herron et al. | 426/490 |
| 5,382,364 A | * | 1/1995 | Bowser et al. | 210/640 |
| 5,938,928 A | * | 8/1999 | Michaels | 210/634 |
| 6,793,825 B2 | * | 9/2004 | Maass et al. | 210/644 |
| 6,848,184 B2 | * | 2/2005 | Cheng | 30/155 |
| 7,566,402 B2 | * | 7/2009 | Thorsen et al. | 210/652 |
| 7,604,746 B2 | * | 10/2009 | Childs et al. | 210/640 |

FOREIGN PATENT DOCUMENTS
JP 57174107 * 4/1982

OTHER PUBLICATIONS

Cath, Tzahi Y. et al., "Forward Osmosis: Principles, Applications, and Recent Developments," Journal of Membrane Science, 2006, pp. 70-87, Elsevier B.V.
McCormick, Peter et al, "Water, Salt, and Ethanol Diffusion Through Membranes for Water Recovery by Forward (Direct) Osmosis Processes," Journal of Membrane Science, 2008, pp. 467-478, Elsevier B.V.
Wick, Gerald L., "Power From Salinity Gradinets," Energy, 1978, vol. 3, pp. 95-100, Pergamon Press, Great Britain.
Moody, C. D. et al., "Forward Osmosis Extractors," Desalination, 1976, vol. 18, pp. 283-295, Elsevier, The Netherlands.
Olsson, Mark S., "Salinity-Gradient Vapor-Pressure Power Conversion," Energy, 1982, vol. 7, No. 3, pp. 237-246, Pergamon Press Ltd., Great Britain.

* cited by examiner

*Primary Examiner* — Ana M Fortuna
(74) *Attorney, Agent, or Firm* — Karen DiDomenicis; Richard Schulte

(57) ABSTRACT

An energy-efficient process for dewatering an aqueous organic solution includes using freely available solar energy to concentrate a draw solution within a reservoir. The draw solution is used in conjunction with a membrane to remove water from the organic solution in a forward osmosis process. The draw solution is diluted by the osmosis process, and returned to the reservoir to be re-concentrated and reused in the osmosis process.

22 Claims, 2 Drawing Sheets

PROCESS FOR DEWATERING AN AQUEOUS ORGANIC SOLUTION

This application is a continuation of U.S. patent application Ser. No. 12/317,163, filed on Dec. 18, 2008 now abandoned.

BACKGROUND OF THE INVENTION

The invention relates to a process for dewatering an aqueous organic solution.

Processes are known for producing high concentration organic solutions such as alcohols useful in the production of alternative fuels. For instance, ethanol suitable for blending with gasoline generally has a concentration of between about 95% and about 100% ethanol by weight and less than about 1% water by volume. Known processes for dewatering ethanol solutions to achieve suitable concentrations include conventional distillation of a fermentation broth to raise the concentration of the broth, until an azeotropic solution is formed. For example, the concentration of ethanol in the broth may be raised using conventional distillation until an azeotrope is formed. The distillation process can be followed by further processing to further remove water from the solution. Such further processing includes distilling at lower than atmospheric pressure in order to derive more ethanol-rich solutions, extractive distillation in which the ethanol solution further includes a separation solvent or extracting agent having a high boiling point and being miscible with the ethanol solution which avoids formation of an azeotrope, and entrainer addition in which the ethanol-water azeotrope can be broken by the addition of a small quantity of benzene or cyclohexane which is followed by a fractional distillation process. Unfortunately, these processes are highly energy intensive. A less energy intensive, alternative process for dewatering solutions uses a highly water selective pervaporation membrane, although heat input is required.

It would be desirable to have a commercially viable, more energy-efficient process for dewatering an organic solution.

SUMMARY OF THE INVENTION

According to one embodiment, the invention is directed to a process for dewatering an aqueous organic solution, comprising the steps of:
  a) providing a membrane having a water/organic selectivity greater than 1 and an osmotic agent rejection rate greater than 95%, the membrane having a draw solution side and a feed solution side;
  b) delivering a feed solution comprising an organic liquid and water having a water activity to the feed solution side of the membrane;
  c) delivering a draw solution comprising an osmotic agent having a water activity lower than the water activity of the feed solution and having a desired concentration from a reservoir to the draw solution side of the membrane whereupon water from the feed solution moves from the feed solution side of the membrane to the draw solution side of the membrane, thereby dewatering the feed solution and diluting the draw solution;
  d) delivering the diluted draw solution from the membrane to the reservoir;
  e) concentrating the draw solution in the reservoir by the use of solar energy to the desired concentration; and
  f) removing the dewatered organic solution from the membrane.

According to another embodiment, the invention is directed to a system for dewatering an aqueous organic solution, comprising:
  a) a source of feed solution comprising an organic liquid and water, the feed solution having a water activity;
  b) a reservoir containing a draw solution comprising an osmotic agent and water, the draw solution having a water activity lower than the water activity of the feed solution, wherein solar energy concentrates the draw solution to a desired concentration within the reservoir;
  c) a membrane having a water/organic selectivity greater than 1 and an osmotic agent rejection rate greater than 95%, the membrane having a draw solution side and a feed solution side;
  d) a means for delivering the feed solution to the feed solution side of the membrane whereupon the feed solution is dewatered;
  e) a means for delivering the draw solution from the reservoir to the draw solution side of the membrane whereupon the draw solution is diluted;
  f) a means for delivering the diluted draw solution from the draw solution side of the membrane to the reservoir; and
  g) a means for removing the dewatered organic solution from the feed solution side of the membrane.

DETAILED DESCRIPTION OF THE INVENTION

Because of the stored mixing potential energy of concentrated solutions containing a water-soluble osmotic agent, herein referred to as draw solutions, such solutions can be used in conjunction with highly selective water/organic membranes to dewater low concentration aqueous organic solutions via forward osmosis, also referred to as direct osmosis. The selectivity of the membrane is the degree to which the membrane allows a particular component or components to permeate the membrane while not allowing other components to permeate the membrane. A highly selective water/organic membrane is selectively permeable to water and impermeable to the organic component of the solution. The aqueous organic solution has higher water activity than the draw solution. Water activity is defined as the ratio of the vapor pressure of water above a sample containing water to the saturation vapor pressure of pure water at the same temperature. Water activity is an indication of the degree to which unbound water is available in a solution. Water moves from an area of higher water activity to an area of lower water activity; therefore water from the aqueous organic solution moves across the membrane to the draw solution, thereby dewatering the organic solution and diluting the draw solution. The draw solution can be stored in a reservoir at a desired concentration suitable to achieve the desired concentration of the aqueous organic solution via forward osmosis. The diluted draw solution, resulting from the forward osmosis process, can be returned to the reservoir. Within the reservoir, water is evaporated from the draw solution through the use of solar energy for re-concentration to the desired concentration.

Figure 1:
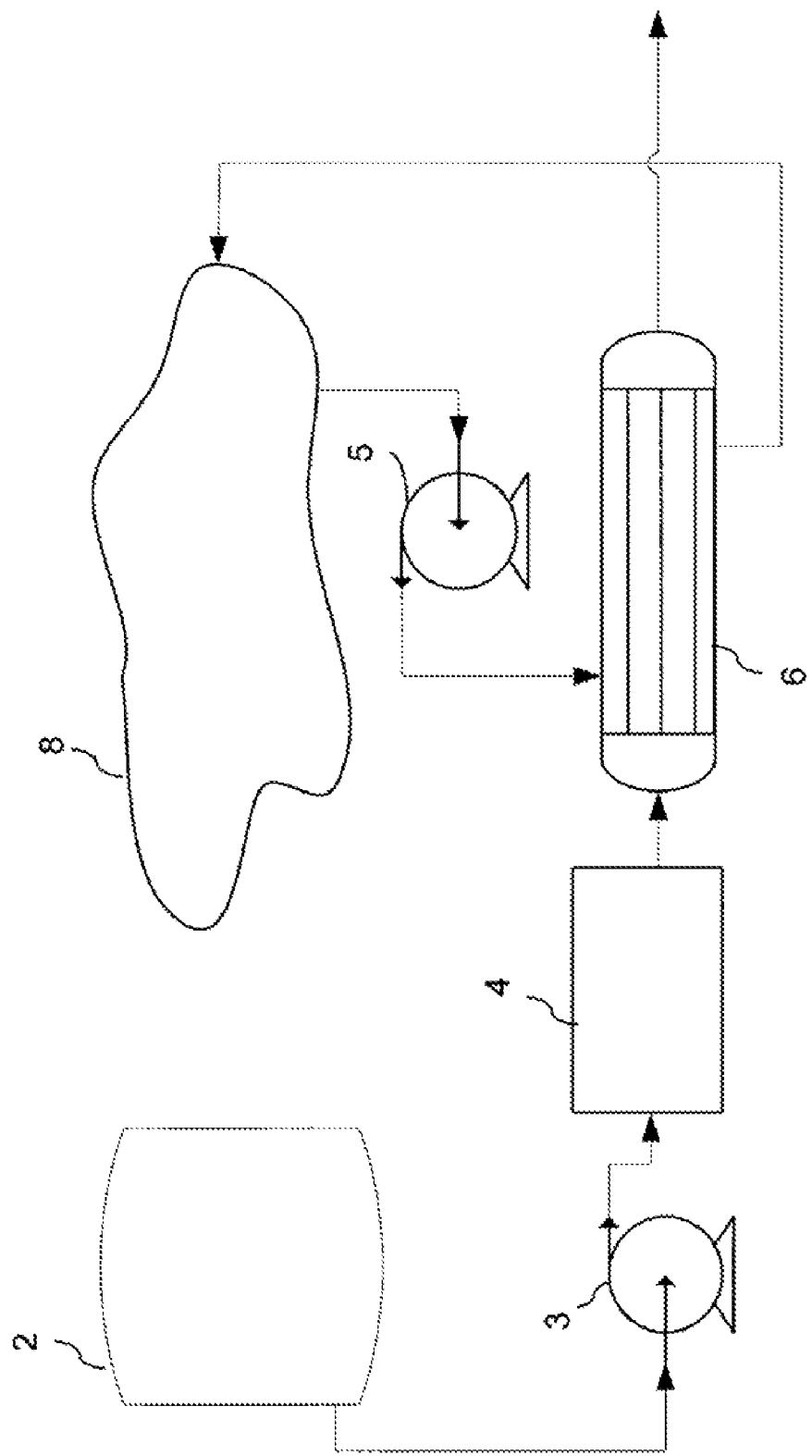
FIG. 1 is a schematic diagram of the process of the invention.

The process of the invention is illustrated in FIG. 1. A feed of the organic solution is delivered from a feed solution source 2 to the feed solution side of a membrane 6. The feed solution source 2 can be a storage tank or a fermentation tank when the organic solution is an alcohol. Draw solution having a lower water activity than that of the feed solution is delivered from a reservoir 8 where it is concentrated to a desired concentration before being fed to the draw solution side of the membrane 6. As a result of the water activity gradient across the membrane, water moves from the feed solution to the draw solution, thus dewatering the organic solution and diluting the draw solution. The resulting dewatered solution can then be removed for desired use, such as incorporation into fuels, transportation to further processing, storage, etc. The diluted draw solution is returned to the reservoir 8 to be re-concentrated using solar energy and recycled to the membrane 6. The feed and draw solutions can be delivered via known means such as piping and pumps. The feed solution can be delivered from the fermentation tank 2 to membrane 6 via gravity feed or pump 3. Similarly, the draw solution can be delivered from reservoir 8 to membrane 6 via gravity feed or pump 5, and the diluted draw solution can be returned to the reservoir via optional gravity feed or pump (not shown).

The aqueous organic feed solution can be an aqueous alcohol solution, e.g., comprising an alcohol having between 2 and 14 carbon atoms, or mixtures or isomers thereof. The aqueous organic solution can be an aqueous ethanol solution. The aqueous organic feed solution can have a concentration between about 0.1% and about 50% by volume, even between about 0.1% and about 15% by volume. As a result of the dewatering process, the resulting organic solution can have a concentration between about 1% and about 99% by volume, even between about 20% and about 99% of volume.

Preferably solids are removed from the feed solution using solids removal means 4 prior to contact with the membrane. Such means can be any appropriate means including filter, centrifuge, gravity settling tank, membrane such as a microporous membrane or a dense membrane, etc. The efficiency of the process can be improved by the use of an ethanol selective membrane for solids removal when the organic solution is an ethanol solution. Optionally, the ethanol selective membrane can be located within the fermentation tank 2.

The process may be run continuously, semi-continuously or as a batch process. If the process is run continuously, the reservoir 8 should be sized to the optimal size to maintain essentially constant concentration of the draw solution stored within the reservoir. By "essentially constant concentration" is meant that the concentration of the draw solution in the reservoir varies somewhat but not so much as to require non-continuous operation. The optimal size of reservoir 8 can be determined knowing the evaporation rate of the draw solution at the atmospheric conditions of temperature, humidity and air velocity. The evaporation rate can be approximated using equation (1), accounting for the various factors mentioned above.

$$E = CT_{atm}^{-0.4} v^{0.5} \left( \frac{P_{sat}(T_{ws})}{T_{ws}} - \frac{RH * P_{sat}(T_{atm})}{T_{atm}} \right) \quad (1)$$

wherein:
E=Evaporation rate of water, (mg/min/cm$^2$)
C=Empirical constant
$T_{atm}$=Atmosphere temperature, K
$T_{ws}$=Surface water temperature, K
v=Velocity of air, m/s
$P_{sat}$=Saturated vapor pressure of the draw solution (kPa)
RH=Relative humidity (fraction)

The process can be run semi-continuously, by which is meant that the delivery of the feed solution to the membrane, the delivery of the draw solution to the membrane and/or the delivery of the diluted draw solution to the reservoir can be run intermittently in order to obtain the aqueous organic solution having the desired concentration.

The draw solution in the reservoir can be open to outdoor atmospheric conditions, such as in a pond or an open tank. The open reservoir is advantageously located in an area where atmospheric conditions are conducive to high evaporation rates, e.g., warm temperature, low humidity and high air velocity. The reservoir can be exposed to direct sunlight during the day. Solar energy is absorbed by the surface of the draw solution in the reservoir which drives the evaporation of the water in the draw solution.

Alternatively, the reservoir can be closed, as in a closed tank. Solar energy can be concentrated with the use of mirrors and/or lenses to heat the draw solution to drive evaporation of the water in the draw solution.

At the desired concentration within the reservoir, the draw solution has sufficient osmotic pressure to extract water from the organic solution through the membrane. The desired draw solution concentration will vary, depending on process parameters such as feed solution concentration, desired product concentration, flow rates, osmotic agent, etc. The higher the osmotic pressure of the draw solution, the greater the ability to extract water from the aqueous organic solution. The draw solution has lower water activity than the organic solution. Water flows from a region of higher water activity to a region of lower water activity. The greater the water activity gradient between the aqueous organic feed solution and the draw solution, the greater the available driving force to move water across the membrane. Saturation concentrations and osmotic pressure gradients for a number of draw solutions containing various osmotic agents when dewatering a 90% ethanol-water solution at room temperature are shown in Table 1.

Suitable osmotic agents for use in the draw solution are those which provide high osmotic pressure or water activity gradient across the membrane. Suitable osmotic agents include halides, nitrates, sulfates, acetates and sugars. As examples which are by no means limiting, sodium chloride, sodium acetate, magnesium nitrate and potassium acetate salts may be used as the osmotic agent. Polyvalent salts may be preferred over monovalent salts as they offer a greater driving force. Urea may also be used as the osmotic agent.

TABLE 1

| Osmotic agent | Saturation Concentration (wt %) | Osmotic pressure gradient (atm) |
| --- | --- | --- |
| Sodium chloride | 26.4 | 360 |
| Potassium chloride | 26.4 | 180 |
| Magnesium chloride | 32.2 | 1090 |
| Calcium chloride | 43.7 | 1700 |
| Ferric chloride | 59.3 | 620 |
| Aluminum chloride | 30.5 | 950 |
| Sodium sulfate | 31.9 | 40 |
| Magnesium sulfate | 26.5 | 50 |
| Ferrous sulfate | 21.1 | −20 |
| Aluminum sulfate | 12.0 | −30 |
| Sodium nitrate | 48.3 | 380 |
| Potassium nitrate | 28.8 | 50 |
| Sucrose | 67.2 | 180 |
| Ammonium bicarbonate | 19.2 | 30 |
| Urea | 26.5 | 290 |
| Ammonium nitrate | 44.4 | 690 |
| Sodium acetate | 60.9 | 180 |
| Potassium acetate | 66.2 | 240 |

The temperature of the draw solution can advantageously be elevated to increase the osmotic agent solubility thereby increasing the osmotic pressure of the draw solution and decreasing the precipitation potential of the osmotic agent. For instance, a saturated sodium chloride solution has an osmotic pressure of about 400 atm at 25° C., about 420 atm at 40° C., and about 440 atm at 55° C. Elevating the temperature of the draw solution also advantageously reduces the viscosity of the draw solution which in turn reduces the energy required to pump the draw solution.

Depending on the draw solution chosen, it may be desirable to utilize pipes which are highly corrosion resistant. Non-corroding, plastic pipes such as PVC pipes are well suited to handle corrosive salt solutions up to a temperature of 60° C. Chlorinated PVC pipes are suited to handle such solutions at higher temperatures.

The selection of the membrane for use in the invention is made after consideration of the requirements for stability, flux and separation efficiency in the forward osmosis process. The membrane has a water/organic selectivity of at least 1. The actual water selectivity can vary depending on the combination of feed and draw solutions being used. When an aqueous alcohol solution is being dewatered, the water/alcohol selectivity is preferably at least about 50. The membrane also has an osmotic agent rejection rate greater than 95%, meaning that membrane prevents at least 95% of the osmotic agent used in the draw solution from moving across the membrane to the feed solution side. A continuous dense membrane with few defects provides a high level of rejection, for example.

Preferably the membrane exhibits long term stability in high concentration environments, and resistance to plasticization by organic solvents. Higher sorption of ethanol in glassy polymers of membranes results in a sharp loss in the separation selectivity of the membrane as a result of plasticization. The use of membranes of higher glass transition aromatic polymers with or without physical (e.g. hydrogen bonding) or chemical (covalent) crosslinks may be favored for plasticization resistance.

The membrane preferably allows high water flux. The water flux of the membrane preferably is at least about one liter per square meter per hour. Water flux is a function of the intrinsic water permeability of the membrane material and the membrane skin thickness. For higher permeability, hydrophilic polymers are desired, having the added advantage of being less prone to membrane fouling. As trans-membrane pressure in forward osmosis is negligible, a minimal support structure is needed for the chosen membrane. Membranes with minimal support structure could be developed for maximum flux.

Another type of membrane that shows potential for forward osmosis is a hybrid organic/inorganic membrane made using a hydrophilic polymer and zeolite. Zeolite nanoparticles have been used in a polyamide matrix to increase water flux. In this membrane design, the zeolites are dispersed into the dense thin film polyamide layer which is formed on a porous support. Alternatively, the zeolite particles can be dispersed in the porous support to increase its hydrophilicity. Additionally, such a design can also provide added strength from the high modulus of the zeolite. Further, zeolite nanoparticles can be used in the dense layer to provide solvent stability (plasticization resistance). Other potential examples of membranes include crosslinked hydrophilic polymers.

The morphology and geometry of the membrane is preferably optimized for the particular separation application as would be within the skill level of one familiar with the use of membranes. Suitable membranes include hollow fiber membranes, flat asymmetric membranes, multicomponent membranes and dense film membranes. Known membrane module configurations for these membrane types can be used. The membrane material can be selected from polymeric materials, metal-organic complexes, inorganic materials and combinations thereof.

The concentration of solute in the boundary layer adjacent the membrane on the draw solution side of the membrane can be lower than the concentration of ethanol in the boundary layer on the feed solution side of the membrane, due to an effect known as dilutive concentration polarization. This effect works to reduce the osmotic pressure driving force across the separating layer of the membrane. To minimize this effect, renewal of the membrane surface at both sides is needed. While this is easily done on the smooth outer side of the separation layer (skin layer) of an asymmetric membrane with a high flow rate, the renewal on the porous side of the skin is more challenging. Thus a thin or highly porous support layer is preferred to minimize the boundary layer thickness and thus maximize the driving force across the membrane. Further, it is envisioned that a thinner boundary layer would be attained with the feed solution contacting the porous side of the asymmetric membrane and the more viscous draw solution contacting the smooth skin surface of the membrane. This configuration could be implemented using asymmetrical flat film in plate-frame or spirally wound membrane modules, or as self-supported hollow fiber membrane modules.

The process according to the invention minimizes energy conversions thus reducing waste due to conversion inefficiencies. The process takes advantage of freely available solar energy to concentrate the draw solution in evaporation ponds built on land that is barren or unsuitable for growing biofuel crops. The solar energy is captured and stored as chemical potential in the draw solution. The storage in the form of evaporation ponds or tanks is inexpensive.

Example

To estimate the energy savings of the invention, a hypothetical reservoir is assumed to be an open evaporation pond located in an area with plenty of sunshine and the following average climatic conditions:

| | |
|---|---|
| Relative Humidity (%) | 52.6 |
| Average Temperature (° C.) | 18.6 |
| Average Wind speed (m/s) | 2.84 |

Figure 2:
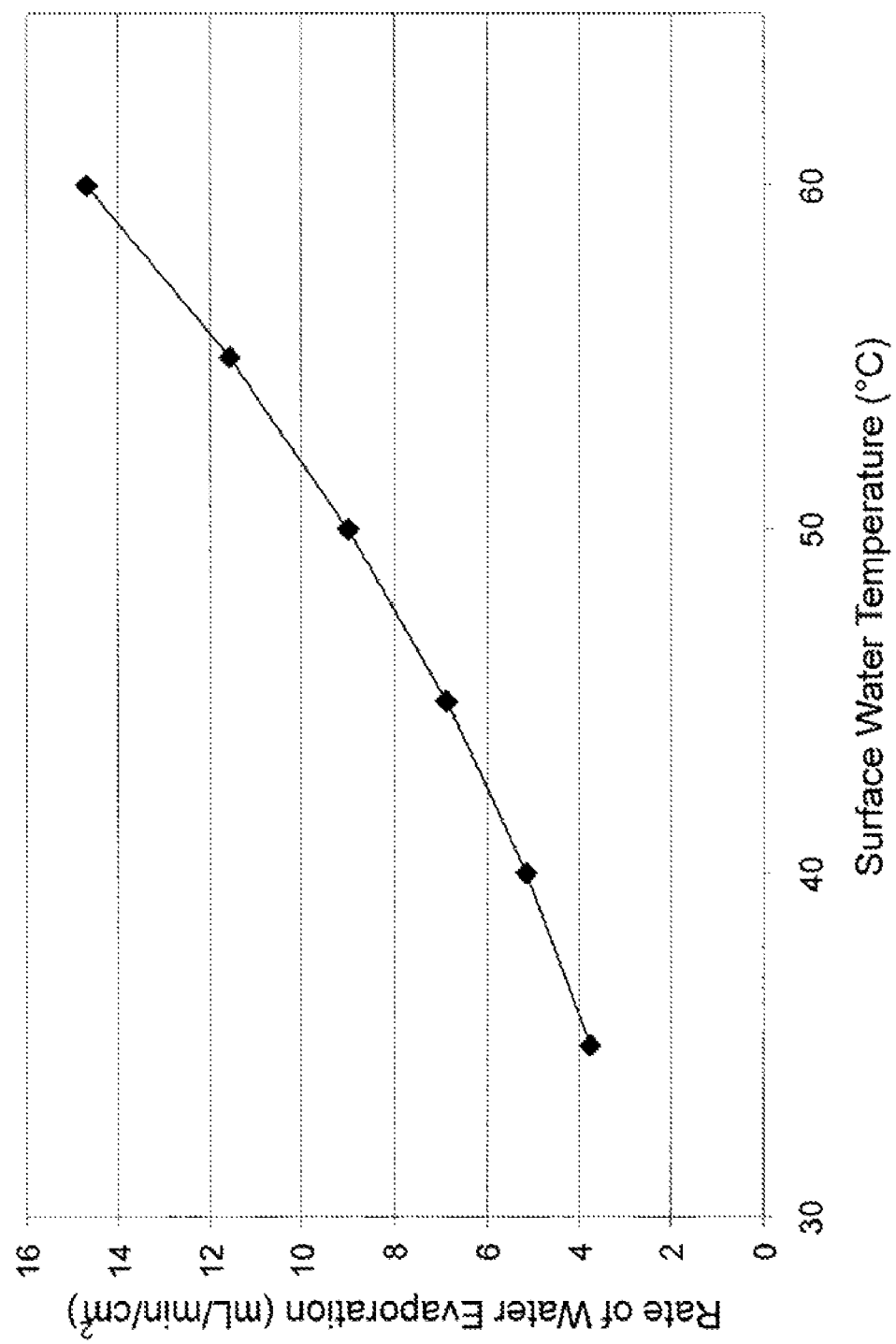
FIG. 2 is a plot of the rate of evaporation of water from the draw solution with changing reservoir surface temperature.

The draw solution is a 20 wt % solution of magnesium chloride in water. Absorbed solar energy leads to a rise in the temperature of the draw solution. FIG. 2 shows the change in evaporation rate with change in temperature on the water surface. FIG. 2 indicates that by allowing solar heating to raise the temperature of water surface to 50° C., approximately 540 mL/hr/cm$^2$ of water can be removed. The pond area was determined by the surface area needed to evaporate water sufficient to attain draw solution concentration of 5M $MgCl_2$ in water.

A cellulose triacetate membrane is used in the osmosis process. The membrane is assumed to be impermeable to ethanol. A water/ethanol separation factor of approximately 95 was assumed to achieve a 99% ethanol recovery.

The effective membrane flux is estimated using a modified flux equation (2) which uses a logarithmic mean driving force for the osmotic pressure.

$$J_w = A_w \left( \frac{(\Delta\pi_1 - \Delta\pi_2)}{\text{Ln}(\Delta\pi_1/\Delta\pi_2)} \right) \quad (2)$$

wherein:
$J_w$=water flux of the membrane
$A_w$=water permeability constant of the membrane
$\Delta\pi_1$=osmotic pressure differential at the inlet of the membrane
$\Delta\pi_2$=osmotic pressure differential at the outlet of the membrane No salt permeation from the draw solution across the membrane and co-current flow are assumed.

The modified flux equation was used to compute the flux based on an assumed water permeability of $3.07\text{E}^{-12}$ m³/m²/Pa/s. The subscripts denote osmotic driving force at positions 1 and 2 of the membrane. The respective osmotic driving force is given in Table 2.

TABLE 2

| Wt % Ethanol - Membrane | FEED SOLUTION | | DRAW SOLUTION | | Osmotic Pressure |
|---|---|---|---|---|---|
| Feed solution side | Water activity | Osmotic Pressure (atm) | Water activity | Osmotic Pressure (atm) | Driving Force (atm) |
| 5 | 0.979 | 26.4 | 0.467 | 1138.8 | 1112.4 |
| 10 | 0.961 | 49.8 | 0.671 | 584.0 | 534.2 |
| 20 | 0.917 | 100.3 | 0.739 | 439.9 | 339.6 |
| 40 | 0.818 | 199.5 | 0.765 | 387.8 | 188.3 |
| 50 | 0.796 | 218.8 | 0.768 | 381.4 | 162.6 |

Based on the modified flux equation and the information in Table 2, the calculated flux for the cellulose triacetate membrane is 553 liter/m²/hr of water permeating through the membrane, resulting in a membrane area requirement of approximately 650 m² (6,982 ft²), assuming a 94.7% water recovery which is required to attain 50 wt % ethanol in the reject stream. This composition is similar to that of an ethanol stream entering the rectifying column from the beer column in a typical ethanol dehydration process.

Estimates of the energy usage by the major equipment in the ethanol dewatering process are given in Table 3. Power consumption by the draw solution pump was simulated in Aspen Plus process simulation software (available from Aspen Technology Inc., Burlington, Mass.).

The energy required to dewater a 5 wt % aqueous ethanol solution to 50 wt % ethanol is significantly lower than that required by a beer column in a conventional distillation process. In comparison, the beer column consumes about 12,000 BTU/gallon of ethanol produced. The energy typically required by distillation for dewatering a 5 wt % aqueous ethanol solution can be estimated as 21,505 BTU/gallon as disclosed in "The Alcohol Textbook" 4th edition, edited by K. A. Jacques, et al. Typically, the beer column consumes about 55% of the total energy consumption in ethanol dewatering, or approximately 12,000 BTU/gallon.

TABLE 3

| | Power (kW) | BTU/hr |
|---|---|---|
| Centrifuge Pump | 49 | 166,310 |
| Centrifuge Decanter | 525 | 1,791,866 |
| Total Centrifuge | 574 | 1,958,176 |
| Draw Solution Pump | 41 | 139,974 |

TABLE 3-continued

| | Power (kW) | BTU/hr |
|---|---|---|
| Total | 615 | 2,098,150 |
| BTU/kg Ethanol Produced | 105 | |
| BTU/gallon Ethanol Produced | 306 | |

What is claimed is:

1. A system for dewatering an aqueous ethanol solution, comprising:
a) a source of feed solution comprising ethanol and water, the feed solution having a water activity;
b) a reservoir containing a draw solution comprising an osmotic agent selected from inorganic salts and acetate salts and water, the draw solution having a water activity lower than the water activity of the feed solution, wherein solar energy concentrates the draw solution to a desired concentration within the reservoir;
c) a membrane having a water/ethanol selectivity greater than 4-50 and an osmotic agent rejection rate greater than 95%, the membrane having a draw solution side and a feed solution side;
d) a means for delivering the feed solution to the feed solution side of the membrane whereupon the feed solution is dewatered;
e) a means for delivering the draw solution from the reservoir to the draw solution side of the membrane whereupon the draw solution is diluted;
f) a means for delivering the diluted draw solution from the draw solution side of the membrane to the reservoir; and
g) a means for removing the dewatered ethanol solution from the feed solution side of the membrane.

2. The system according to claim 1 wherein the feed and draw solutions are delivered continuously to the feed and draw solution sides of the membrane, respectively, and the reservoir is sized such that the concentration of the draw solution in the reservoir is essentially constant.

3. The system according to claim 1 further comprising a means for removing solids from the feed solution prior to delivering to the membrane.

4. The system according to claim 3 wherein the means for removing solids is a filter, a centrifuge, a microporous membrane or a dense membrane.

5. The system according to claim 4 wherein the dense membrane is an ethanol selective membrane.

6. The system according to claim 1 wherein the membrane is selected from the group consisting of hollow fiber membranes, flat asymmetric membranes, multicomponent membranes and dense film membranes and wherein the membrane comprises a material selected from the group consisting of polymeric materials, metal-organic complexes, inorganic materials and combinations thereof.

7. The system according to claim 1 wherein the means for delivering the feed solution to the membrane and the means for delivering the draw solution to the membrane comprise pumps or gravity.

8. The system according to claim 1 wherein the means for delivering the draw solution to the membrane and the means for delivering the diluted draw solution to the reservoir comprise non-corroding plastic piping.

9. The system according to claim 1 wherein the reservoir is a pond or an open tank.

10. A process for dewatering an aqueous ethanol solution, comprising the steps of:
   a) providing a membrane having a water/ethanol selectivity greater than 50 and an osmotic agent rejection rate greater than 95%, the membrane having a draw solution side and a feed solution side;
   b) delivering a feed solution comprising ethanol and water having a water activity to the feed solution side of the membrane;
   c) delivering a draw solution comprising an osmotic agent selected from inorganic salts and acetate salts having a water activity lower than the water activity of the feed solution and having a desired concentration from a reservoir to the draw solution side of the membrane whereupon water from the feed solution moves from the feed solution side of the membrane to the draw solution side of the membrane, thereby dewatering the feed solution and diluting the draw solution;
   d) delivering the diluted draw solution from the membrane to the reservoir;
   e) concentrating the draw solution in the reservoir by the use of solar energy to the desired concentration; and
   f) removing the dewatered ethanol solution from the membrane.

11. The process according to claim 10 wherein the feed solution has a concentration between about 0.1% and about 50% by volume.

12. The process according to claim 10 wherein the feed solution has a concentration between about 0.1% and about 15% by volume.

13. The process according to claim 10 wherein the dewatered ethanol solution has a concentration of between about 1% and about 99% by volume.

14. The process according to claim 10 wherein the draw solution comprises a water-soluble component selected from the group consisting of halides, nitrates, phosphates, sulfates and acetates.

15. The process according to claim 10 wherein the membrane has a flux of at least about 1 $L/m^2/hr$.

16. The process according to claim 10 wherein the feed and draw solutions are delivered continuously to the feed and draw solution sides of the membrane, respectively and wherein the reservoir is sized such that the concentration of the draw solution in the reservoir is essentially constant.

17. The process according to claim 10 wherein the feed and draw solutions are delivered semi-continuously or batchwise to the feed and draw solution sides of the membrane, respectively.

18. The process according to claim 10 wherein the membrane is selected from the group consisting of hollow fiber membranes, flat asymmetric membranes, multicomponent membranes and dense membranes, and wherein the membrane comprises a material selected from the group consisting of polymeric materials, metal-organic complexes, inorganic materials and combinations thereof.

19. The process according to claim 10 further comprising removing solids from the feed solution prior to delivering the feed solution to the membrane.

20. The process according to claim 10 wherein the reservoir is open to the atmosphere and solar energy drives evaporation of the water in the draw solution.

21. The process according to claim 10 wherein solar energy is concentrated with the use of mirrors and/or lenses to heat the draw solution in the reservoir.

22. The process according to claim 10 wherein the draw solution comprises urea.

\* \* \* \* \*